(12) United States Patent
Coors (10) Patent No.: US 10,145,016 B2
(45) Date of Patent: Dec. 4, 2018

(54) REACTOR-SEPARATOR ELEMENTS

(71) Applicant: W. Grover Coors, Golden, CO (US)

(72) Inventor: W. Grover Coors, Golden, CO (US)

( * ) Notice: Subject to any disclaimer, the term of this patent is extended or adjusted under 35 U.S.C. 154(b) by 267 days.

(21) Appl. No.: 15/339,174

(22) Filed: Oct. 31, 2016

(65) Prior Publication Data
US 2017/0370010 A1 Dec. 28, 2017

Related U.S. Application Data

(60) Provisional application No. 62/355,663, filed on Jun. 28, 2016.

(51) Int. Cl.
| | | |
|---|---|---|
| *C01B 3/40* | (2006.01) | |
| *C01B 3/50* | (2006.01) | |
| *C01C 1/04* | (2006.01) | |
| *C07C 2/80* | (2006.01) | |
| *C25B 1/10* | (2006.01) | |
| *B01D 53/22* | (2006.01) | |
| *B01D 53/32* | (2006.01) | |

(Continued)

(52) U.S. Cl.
CPC ............ *C25B 1/10* (2013.01); *B01D 53/228* (2013.01); *B01D 53/326* (2013.01); *B01D 69/046* (2013.01); *C01B 3/40* (2013.01); *C01B 3/501* (2013.01); *C01B 3/503* (2013.01); *C01C 1/0494* (2013.01); *C07C 2/80* (2013.01); *C25B 11/02* (2013.01); *C25B 13/02* (2013.01); *H01M 8/0618* (2013.01); *H01M 8/0656* (2013.01); *B01D 2053/221* (2013.01); *C01B 2203/0233* (2013.01); *C01B 2203/0405* (2013.01); *C01B 2203/1058* (2013.01); *C01B 2203/1241* (2013.01); *C07C 2529/06* (2013.01)

(58) Field of Classification Search
CPC ........... C25B 1/10; C25B 11/02; C25B 13/02; B01D 69/046; B01D 53/228; B01D 53/326; B01D 2053/221; C01B 3/503
See application file for complete search history.

(56) References Cited

U.S. PATENT DOCUMENTS

| | | | |
|---|---|---|---|
| 6,168,650 B1 | 1/2001 | Buxbaum | |
| 6,942,767 B1 * | 9/2005 | Fazzina | C02F 1/46104 204/242 |

(Continued)

FOREIGN PATENT DOCUMENTS

| | | |
|---|---|---|
| CN | 101134158 A | 3/2008 |
| WO | 99/25649 A1 | 5/1999 |

OTHER PUBLICATIONS

Burkanov, G. S. et al., Palladium-Based Alloy Membranes for Separation of High Purity Hydrogen from Hydrogen-Containing Gas Mixtures, Platinum Metals Rev., 2011, pp. 3-12, vol. 55, No. 1.

(Continued)

*Primary Examiner* — Nicholas A Smith
(74) *Attorney, Agent, or Firm* — Larson & Anderson, LLC (57) ABSTRACT

Reactor/separator elements for performing the generation and/or separation of hydrogen gas with improved efficiency have a central core and a separation layer that, in combination, define at least one spiral gas flow channel extending from one end of the central core to the opposite end of the central core. In use, the reactor/separator element may be placed in a housing which constrains gas on the outside of the reactor/separator element into the spiral channel defined by the outside of the separation layer.

20 Claims, 6 Drawing Sheets

(51) Int. Cl.
*B01D 69/04* (2006.01)
*C25B 11/02* (2006.01)
*C25B 13/02* (2006.01)
*H01M 8/0612* (2016.01)
*H01M 8/0656* (2016.01)

(56) References Cited

U.S. PATENT DOCUMENTS 8,845,768 B2 9/2014 Wachsman et al.
2004/0129135 A1 7/2004 Roark et al.
2007/0251389 A1 11/2007 Katsir et al.
2013/0288150 A1 10/2013 Hodges et al.

OTHER PUBLICATIONS

Phair, J. W. et al., Review of proton conductors for hydrogen separation, Ionics, 2006, pp. 103-115, vol. 12, DOI 10.1007/s11581-006-0016-4.

* cited by examiner

REACTOR-SEPARATOR ELEMENTS

RELATED APPLICATIONS

This application claims the benefit under 35 USC § 119 of U.S. provisional application No. 62/355,663 filed Jun. 28, 2016, which application is incorporated herein by reference in its entirety.

FIELD OF THE INVENTION

This application relates to reactor/separator elements of a type useful for the production and/or separation of hydrogen gas. The reactor/separator elements make use of a separation layer that is selectively permeable to hydrogen or a proton conducting matrix to separate hydrogen from a gas stream flowing through a spiral gas flow path.

BACKGROUND OF THE INVENTION

Figure 1:
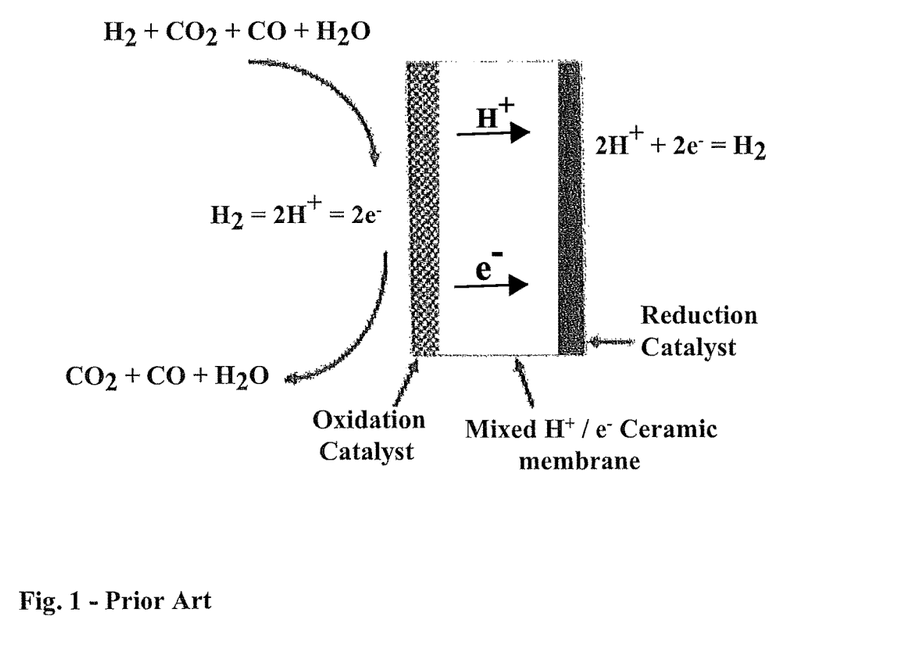
FIG. 1 shows a schematic representation of a process for $H_2$ separation using a mixed proton/electron conducting membrane.

Hydrogen gas has the potential to be a significant fuel source in meeting the energy demands of the future. Various processes for production and/or separation of hydrogen to provide a sufficiently pure hydrogen gas to act as a fuel are known. For example, as shown in FIG. 1, hydrogen gas can be separated from a mixture of $CO_2$, CO, and water vapor using a mixed proton/electron conducting membrane. Phair, J. W and Badwal, S. P. S, *Ionics* (2006) 12: 103-115. Hydrogen gas can also be formed in a process such as steam-methane reforming (SMR) or a water gas shift (WGS) reaction of CO and water to form CO2 and hydrogen gas and then separated from the resulting gas mixture using a proton conducting membrane. See for example U.S. Pat. No. 8,845,768. Palladium-based membranes are also known to be useful for separation of hydrogen gas. Burkhanov et al., *Platinum Metals Rev.* (2011) 55: 3-12.

SUMMARY OF THE INVENTION

The present application relates to reactor/separator elements for performing the generation and/or separation of hydrogen gas with improved efficiency. The reactor/separator element of the invention comprises (a) a central core comprising a gas permeable material, said central core being shaped on the outer surface thereof to define at least one spiral channel extending from a first end of the central core to a second, opposed end of the central core;

(b) a separation layer, disposed on the central core and conforming to the shape of the outer surface of the central core element, said separation layer being formed from a material that is impermeable to gases other than hydrogen selected from the group consisting of (1) materials that are permeable to hydrogen species under pressure; (2) mixed ionic electronic conductors that are permeable to protons in the absence of an applied potential difference, and (3) proton conducting materials that are permeable to protons in response to an applied potential difference; and optionally, (c) an outer layer disposed on the separation layer, said outer layer comprising a gas permeable material. The central core and the separation layer, in combination, define at least one spiral gas flow channel extending from the first end of the central core to the second end of the central core.

In use, the reactor/separator element may be placed in a housing which constrains gas on the outside of the reactor/separator element into the spiral channel defined by the outside of the separation layer.

DETAILED DESCRIPTION OF THE INVENTION

The present application relates to reactor/separator elements, of a type useful for the production and/or separation of hydrogen gas.

Structure of a Reactor/Separator Element

Figure 2:
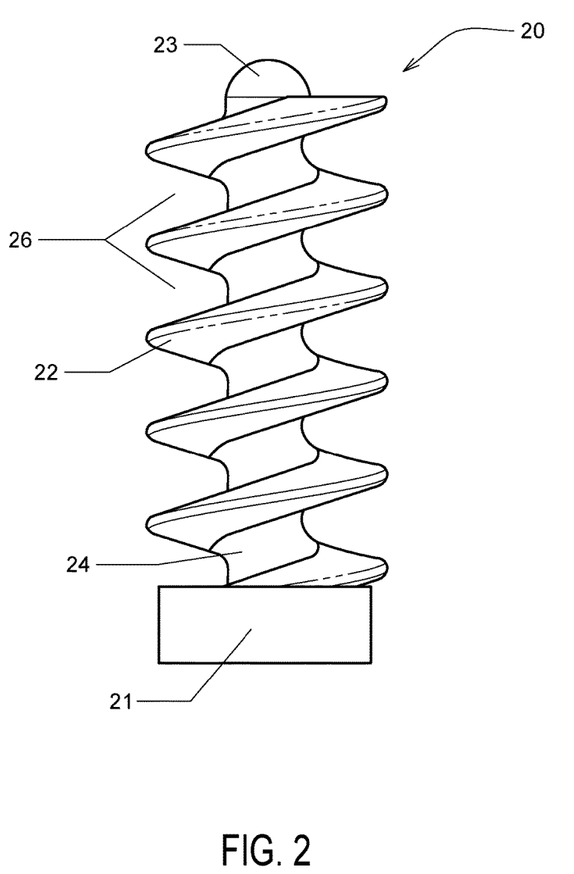
FIG. 2 shows a side exterior view of reactor/separator element in accordance with the invention.

As shown in FIG. 2, in one embodiment, a reactor/separator element 20 in accordance with the invention has a helical flange 22 wrapped around a central core 24. The helical flange 22 defines a spiral channel 26, in which gases flow from one end of the reactor/separator element 20 when the reactor/separator element is disposed within a housing. In the embodiment shown in FIG. 2, one end 21 of the central core 24 is open, while the other end 23 is capped such that gas flow from the central core is only possible in one direction.

The central core 24 is formed from a gas permeable material, and may in some embodiments have a central opening as indicated by dashed lines in FIG. 2. The central core is shaped on the outer surface thereof to define at helical flange and hence the spiral channel. extending from a first end of the central core to a second, opposed end of the central core. Suitable examples for the material of the central core are materials that will withstand the high reaction temperatures (in excess of 300° C.) and remain inert to the reactants used and products formed. Further, it is desirable to have a material that can be readily formed into a gas permeable body using conventional techniques such as ceramic green forming processes including slip casing, jiggering, injection molding and green machining. Materials that have these properties include porous ceramic/metal cermet consisting of about 40 vol % ceramic phase, for example, BZCY ceramics such as $BaZr_xCe_{0.9-x}Y_{0.1}O_{3-d}$ (0≤x≤0.9), about 40 vol % metal phase, for example nickel or copper metal and balance of open porosity. Such a central core is electrically conductive, serving as the electrode where hydrogen is produced on the permeate (downstream) side of the membrane. In instances where electrical conductivity is not required, the central core may consist substantially of a porous ceramic material, such as partially-stabilized zirconia, YSZ, or barium (strontium) cerate-zirconate, where the material composition is selected in order to be compatible with the mechanical and chemical properties of the dense separator membrane.

A separation layer is disposed on the central core and conforms to the shape of the outer surface of the central core. The separation layer is formed from a material selected that will allow the selective passage of hydrogen (either as hydrogen species including hydrogen gas or as protons), and specifically of a material selected from the group consisting of (1) materials that are permeable to hydrogen species under pressure; (2) mixed ionic/electronic conductors that are permeable to protons in the absence of an applied potential difference, and (3) proton conducting materials that are permeable to protons in response to an applied potential difference. As used herein, a material is selective for passage of hydrogen gas if, at the operating conditions of a reaction, greater than about 0.1 standard $cm^3$/min of nominally pure hydrogen is obtained per square centimeter of membrane separator area, and preferably greater than 1.0 standard $cm^3/min/cm^2$.

Materials that are permeable to hydrogen under pressure include metals and alloys, including palladium, and various palladium alloys. These include, without limitation, palladium based alloys containing silver, yterrbium, copper, ruthenium, and mixtures of ruthenium and indium. When a material of this type is used as the separation layer, it can be applied to the outer surface of the central core to provide a layer of consistent thickness using known techniques such as electroplating, sputtering and chemical-vapor deposition. The thickness of separation layers of this type is suitably 1 to 10 microns.

Mixed ionic-electronic conductors that are permeable to protons in the absence of an applied potential difference are also known. Examples include lanthanum tungstate and lanthanum niobate. Yttrium-doped barium zirconate-cerate BZCY is a mixed conductor of protons, oxygen ion vacancies, electrons and electron holes, and can be used as the separation layer as well as the central core by depositing it in greater density in the separation layer and providing hydration to the separation layer.

The separation layer may also be formed from a proton-conducting material that is permeable to protons in response to an applied potential difference. Examples of specific materials include without limitation, alkaline-earth cerate- and zirconate-based perovskite materials such as acceptor doped $SrCeO_3$, $BaCeO_3$ and $BaZrO_3$, and various solid solutions of these. The proton conductivity is greater than about 1 mS/cm, and preferably greater than about 3 mS/cm, with proton transference number greater than about 0.9.

In embodiments in which the separation layer depends on a potential difference between the two sides of the separation layer, the central core suitably contains a conductive component, such as a metal, in an amount sufficient to allow the central core to act as an electrode. (Where permeation of hydrogen is inward, the central core would act as the electrode where the reaction, $2H^++2e^-=H_2$, takes place.) Metals included for this purpose may or may not be catalytically active. Suitable materials for this purpose include nickel, copper, silver, gold and various alloys.

Depending on the intended mode of operation, the reactor/separator element of the invention may or may not include an outer layer disposed on the separation layer. The outer layer, if present, may have a substantially constant thickness and conform in shape to the underlying separation layer. Alternatively, the outer layer may fill some, or all, of the spiral channel between the helical flanges. The degree to which the spiral channel is filled may be different in different parts of the spiral channel, for example filling an increasingly greater portion of the channel as the channel proceeds from one end of the reactor/separator element to the other.

For example, in embodiments where the separation layer requires the application of a potential difference for hydrogen permeation to occur, the outer layer is present and serves as an electrode. The material of this outer layer is gas permeable, to allow passage of hydrogen to the separation layer, and conductive, providing the function of the electrode for the reaction, $H_2=2H^++2e^-$.

In some embodiments of the invention, a hydrogen generating reaction occurs in the spiral channel, and the hydrogen is separated out via the separation layer. In this case, the outer layer may be present, regardless of the nature of the separation layer, and contain or be in direct contact with a catalyst. Alternatively, a reaction layer, for example composed of a zeolite catalyst may be provided exterior to the outer layer. The reaction layer does not, however, have to be integral to the reactor/separator element, and could for example be separate or associated with a housing, which serves only to enclose some portion of the spiral channel.

Figure 3:
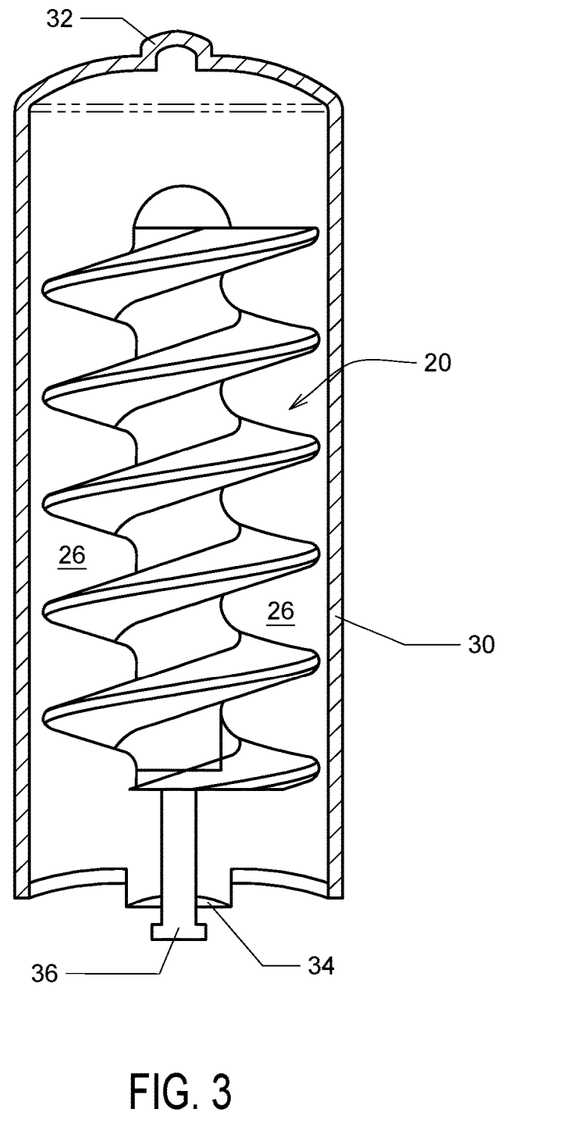
FIG. 3 shows a reactor/separator element 20 disposed within a housing 30, with the housing shown as a cut away to expose the reactor/separator element.

FIG. 3 shows a reactor/separator element 20 disposed within a housing 30, with the housing shown as a cut away to expose the reactor/separator element. In the embodiment as shown, the interior surface of the housing 30 is proximate to the helical flange 22, such that gas flow from one end of the reactor/separator element is at least substantially constrained to the spiral flow channel 26 between the helical flanges. The interface between the spiral flange and the housing need not be gas tight. In some embodiments, a compliant permeable pad, for example of nickel felt or quartz wool is disposed in the space between the housing and the helical flanges. A pliant foil layer can also be used as a gasket. The housing 30 has a fitting 32 and a fitting 34 through which gaseous materials can be introduced to, and removed from, the housing. Fitting 36 provides connection for removal of gases generated in the central core.

In its most general use, a mixed gas containing hydrocarbons and/or steam is introduced into the spiral channel 26 within the housing 30 under conditions such as elevated temperature under which hydrogen gas selectively permeates from the spiral channel 26 through the separation layer and into the central core from which it can be recovered as a purified gas stream. In the alternative, since the inside of the helical flange also defines a spiral channel, the direction of hydrogen permeation could be reversed by changing the gas flows introduced and collected in the central core. Thus, in general, the collection side, whether on the inside or outside of the separator will be on the opposite side of where any reaction occurs.

Figure 5:
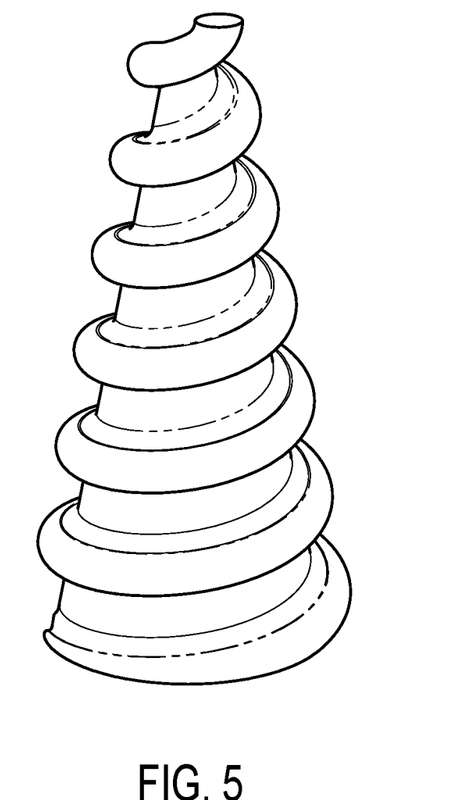
FIG. 5 shows a conical reactor/separator element.
Figure 6:
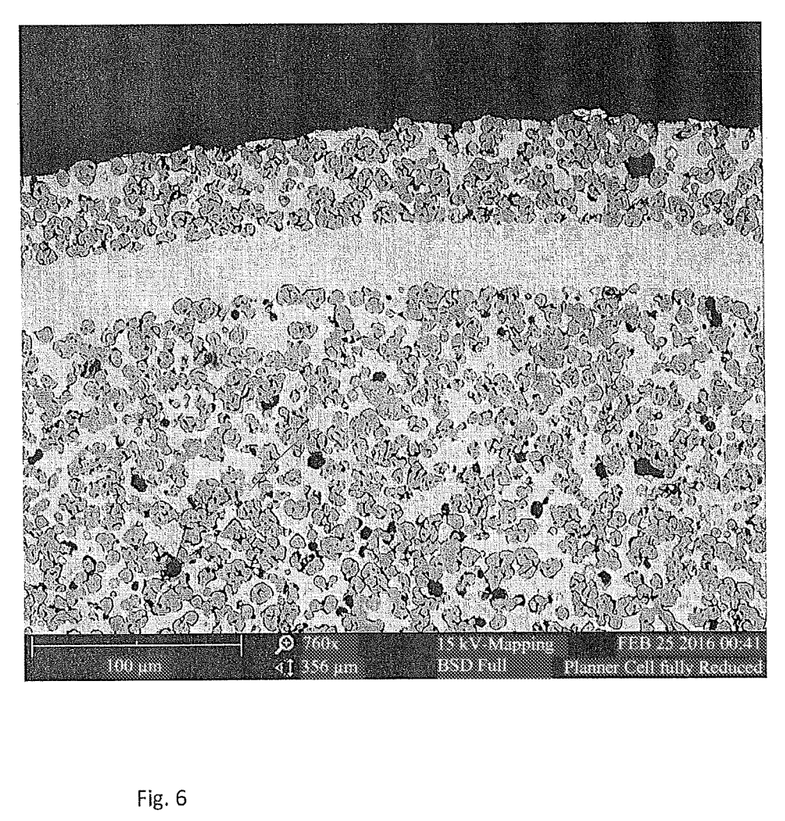
FIG. 6 shows a cross section of a ceramic membrane with a central core, a separation layer and an outer layer.

While the reactor/separator element discussed above is nominally cylindrical, the reactor/separator element of the invention can take other forms. For example, the reactor separator element may be conical in shape as shown in FIG. 5. Such a reactor/separator element can be used in a conical housing, for example one that conforms in shape to the conical reactor/separator element.

Advantages of the Structure of the Invention

Figure 4:
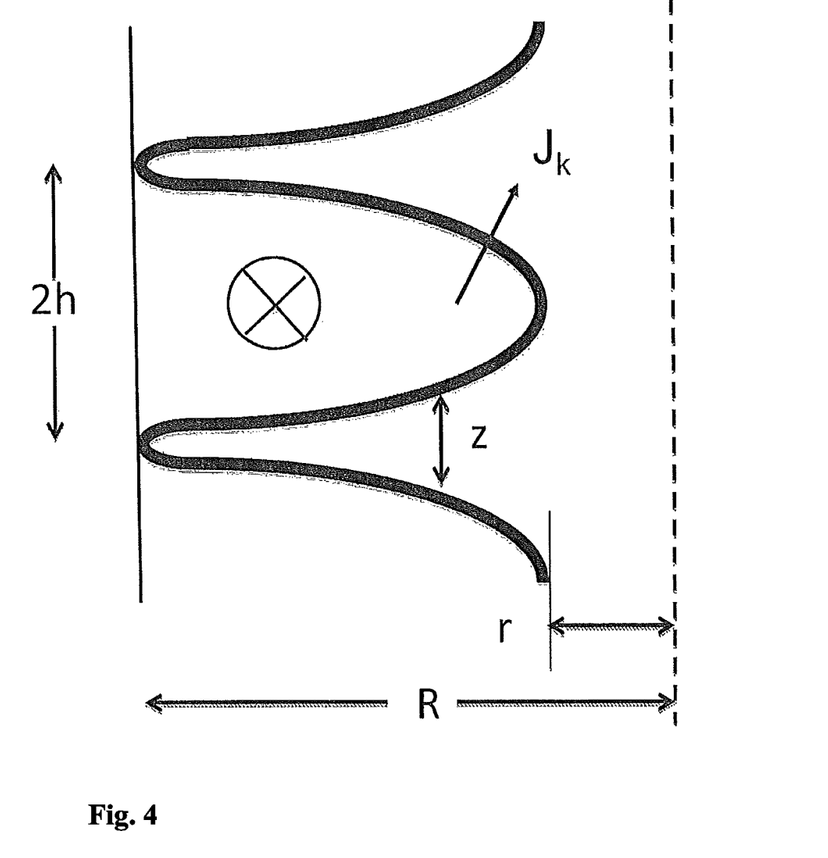
FIG. 4 shows a cross-section through two adjacent flanges of a helical reactor/separator element in which the spiral flow channel is contoured for constant cross-sectional radial area.

The reactor/separator element of the present invention offers advantages over tubular reactors, as known in the art. One advantage of a spiral channel associated with helical flanges is the increase in amount of surface area per unit length of a cylinder or tube with and without the helical surfaces. FIG. 4 shows the cross section of a cylinder having helical flanges. The dashed line corresponds to the center line of the central core. The cylinder outside diameter without flanges is 2r, and the diameter with flanges is 2R. The length of the tube segment extended by the flange is 2h. The additional surface area of the flanges may be approximated by the surface area of a frustum (times 2).

$$A = 2\pi(R+r)\sqrt{(R-r)^2 + h^2} \quad (1)$$

The equivalent membrane area of a length 2h of a straight-walled tube with outside diameter 2r would simply be 2πrh. For the case where R=2r=2h, the ratio of the membrane area with and without flanges is $$\frac{3\sqrt{2}}{2} = 2.12.$$

The helical membrane depicted on the left in FIG. 2 has 4.7 times more surface area per unit length than a straight wall tube with the same minor outside diameter. The practical result is that the surface area of a straight-walled cylindrical membrane of a given length can be increased significantly by providing helical flanges on the outside diameter. The same effect is also obtained if one considers the inside surface of helical flanges.

The shape of the flanges can also be tailored in a manner not available to or required for a tubular reactor or separator. The flux of hydrogen depends on bulk material properties, such as diffusivity and electrical conductivity, which determine the concentration gradient of a species diffusing through a membrane. For any give concentration gradient, the flux is determined on the basis of cross sectional area normal to the flow of the species in the core. In the case of a straight-walled tube, the direction of the flux in the radial direction is always perpendicular to membrane surface. But with a helical membrane, this is not the case, and provision can be made for the fact that membrane flux and radial flux vectors are not co-linear. In cylindrical coordinates, the area of an annulus of height, z, decreases with decreasing radius. The surface contour of the helical flanges can be designed to compensate for this. For example, it may be advantageous to design the contour so that the area of the annulus normal to the radial direction, as depicted in FIG. 4, is independent of R, where the area of the annulus at some radius, R, is 2πRz. This may be accomplished if the height of the annulus, z, is proportional to 1/R. It is also possible to design the contour so that the cross-sectional area of the annulus actually increases with decreasing radius. Without controlling the surface contour, diffusing species or electrical currents on the inside of the membrane may be non-uniform and become constricted by the decreasing cross-sectional area upon moving from the outside to the inside of the membrane. In FIG. 4, the flow of permeant from which hydrogen is to be separated is indicated by the arrow tip that extends into the page, parallel to the flange surface. The flux of hydrogen that diffuses through the membrane is indicated by the vector arrow, $J_k$ that extends in the plane of the paper and perpendicular to the surface of the membrane surface. The heavy line represents the helical membrane flanges and the light line is the enclosing boundary, for example as created by a housing.

The shape of the surface with the helical flanges can also be varied from one end of the reactor/separator element to the other. This can be used to compensate for two different effects. When the reactor/separator element is used only as a separator, the amount of hydrogen gas in the input gas mixture decreases with distance along the flow path. In a reactor, the chemical equilibrium of species in the permeant is shifted due to selective removal of one of the species. The flux of diffusing species through the membrane typically depends on the local partial pressure of the gas phases, and therefore, changes continually along the length of the spiral channel. An example is steam-methane reforming, where a mixture of steam ($H_2O$) and methane ($CH_4$) is introduced at the entrance of the flow channel (in the presence of nickel catalyst), hydrogen ($H_2$) and a mixture of carbon monoxide (CO) and carbon dioxide ($CO_2$) are produced as the reacting gas mixture flows down the channel. If the membrane is selective to hydrogen diffusion, then as hydrogen is extracted, chemical equilibrium is shifted towards production of $CO_2$, more steam is consumed, and the partial pressure of hydrogen in the permeant decreases. Furthermore, the hydrogen flux through the membrane at any position along the channel is orthogonal to the membrane surface and the direction of permeant flow. Also, for gaseous permeant, as any species is extracted, the volume of remaining gas decreases along the flow path, and the space velocity of the remaining gas correspondingly decreases. In order to control the space velocity of permeant, it may be beneficial to alter the contour of the channel either by adjusting the flange shape, flange pitch, or introducing an overall taper to the helical membrane device as shown in FIG. 5. The utilization of helical surfaces allows the use of engineered contours and channel configurations to address these issues in a way that cannot be achieved using a standard tubular configuration.

Reactor/Separator Element for Steam-Methane Reforming

Steam methane-reforming is a common process for production of bulk hydrogen. At high temperatures (400-800° C.) and in the presence of a metal-based catalyst (for example, nickel), steam reacts with methane to yield carbon monoxide and hydrogen in accordance with the reaction:

$$CH_4 + H_2O \rightleftharpoons CO + 3H_2.$$

Additional hydrogen gas can be generated by performing a water-gas shift reaction:

$$CO + H_2O \rightleftharpoons CO_2 + H_2.$$

To use the reactor/separator element of the invention in a steam/methane reforming process, the catalyst, such as nickel, is suitably incorporated into an outer layer, or an additional layer of gas permeable material disposed over the outer layer.

Production of Hydrocarbons

Hydrocarbons, such as ethylene and benzene, may be produced from dry methane in a catalytic membrane reactor by dehydrogenation with hydrogen extracted from the feed gas. In the case of MDA (methane dehydroaromatization), there is no steam introduced with the methane. The overall desired reaction is $6CH_4 = C_6H_6 + 9H_2$. This is carried out along the flow channel with specialized zeolite catalysts. Copper electrodes are required in this case to keep methane from pyrolysing on the metal instead of in the catalyst. The structure is identical, otherwise.

Production of Ammonia

Ammonia can be synthesized by permeating hydrogen through the membrane of the reactor/separator of the invention and then reacting the permeate hydrogen with nitrogen, for example in a process called solid-state ammonia synthesis (SSAS). In SSAS, nitrogen is admitted to one side of the membrane and water vapor, for example, is admitted to the other side. The water vapor dissociates into protons and oxygen, an external voltage drives the protons through the membrane, and the nitrogen and protons react on the nitrogen side of the membrane to form $NH_3$. In this process, $H_2$ could also come from methane, biogas, steam electrolysis or simply carried over from some other industrial process—such as recovered hydrogen from silane in semiconductor processes or metal refining. As of today, a lot of work is going into development of catalysts that break nitrogen bonds. The advantage of the membrane reactor is that hydrogen percolates to the surface as protons, so in theory, once the nitrogen bond is broken, ammonia forms with ease.

Production of Hydrogen Gas by Steam Electrolysis.

$H_2$ can be produced from water vapor by steam electrolysis in a protonic ceramic electrolysis cell (PCEC). In this case, an oxidation-tolerant electrode (like LSCF or BSCF) is required on the steam side. Hydrogen is driven galvanically through the separator, and $O_2$ and residual steam flows down the spiral channel. Otherwise, the reactor is basically the same design.

Production of Electric Power by a Fuel Cell.

$H_2$ can be consumed in a protonic ceramic fuel cell (PCFC). In this case, an oxidation-tolerant outer electrode (like LSCF or BSCF) is required. Hydrogen is driven through the separator and $O_2$, typically from air, reacts with the hydrogen producing an electric potential. Residual steam and air flow down the spiral channel. Otherwise, the reactor is basically the same design.

EXAMPLE

An example of a protonic ceramic membrane is shown in FIG. 5 in cross-section. The light band, approximately 25 microns thick, is the actual dense protonic ceramic electrolyte membrane, which conducts protons, but in impermeable to hydrogen and other gases. It is supported on the bottom by a thick composite electrode consisting of BZCY (light phase) and Ni (dark phase). The shape of this composite support can be prepared to suit the device architecture desired, only limited by the range of ceramic green forming processes such as slip casing, jiggering, injection molding and green machining. The electrode is electrically conducting and porous for permeate gas percolation. The thinner top layer is the outer electrode—also a composite of Ni/BZCY cermet. For construction as a helical membrane, a continuous coating of the BZCY electrolyte is applied to the outside surface of the helical structure shown in FIG. 2, formed from the Ni/BZCY composite material. The outer electrode layer is subsequently applied by spray coating or dipping. The resulting complete structure is then typically cofired.

The invention claimed is:

1. A reactor/separator element comprising:
   (a) a central core comprising a gas permeable material, said central core being shaped on the outer surface thereof to define at least one spiral channel extending from a first end of the central core to a second, opposed end of the central core;
   (b) a separation layer, disposed on the central core and conforming to the shape of the outer surface of the central core element, said separation layer being formed from a material selected from the group consisting of (1) materials that are permeable to hydrogen gas under pressure; (2) mixed ionic electronic conductors that are permeable to protons in the absence of an applied potential difference, and (3) proton conducting materials that are permeable to protons in response to an applied potential difference; and
   optionally, (c) an outer layer disposed on the separation layer, said outer layer comprising a gas permeable material,
   wherein the central core and the separation layer, in combination, define at least one spiral gas flow channel extending from the first end of the central core to the second end of the central core.

2. The reactor/separator of claim 1, wherein the contour of the helical surfaces is such that the cross-sectional area in the radial direction is a specified function of the radius, and more specifically, such that the said cross-sectional area is constant with radius.

3. The reactor/separator of claim 1 where the cross-section of the flow channel formed by the enclosed helix is shaped to control the space velocity of permeant gas along the length of the spiral channel.

4. The reactor/separator of claim 1, constructed substantially of ceramic and ceramic composites.

5. The reactor/separator element of claim 1, wherein the separation layer is a dense film of ionically-conducting ceramic coating of about from 10 nanometers to 50 microns in thickness attached to a porous ceramic support.

6. The reactor/separator element of claim 5, wherein the separation layer is comprises a ceramic proton-conductor or a composite material containing a ceramic proton conductor for the purpose of separating hydrogen gas from a mixture of hydrogen and other gases.

7. The reactor/separator element of claim 5, wherein the separation layer comprises a solid solution with end members $BaCe_{(1-x)}M_xO_{3-d}$ and $BaZr_{(1-x)}M_xO_{3-d}$, where M is a $4^+$ cation from the group including yttrium, gadolinium, samarium, lanthanum and other actinides, and the stoichiometric coefficient, d, ranges from about 0.05 to 0.20.

8. The reactor/separator element of claim 1, wherein the separator layer is a thin, dense membrane applied to a porous ceramic support of the same material or a composite of the same ceramic material and a metallic phase.

9. The reactor/separator element of claim 1, wherein the separator layer comprises palladium, palladium alloys, vanadium, tungsten, molybdenum and alloys known to be permeable to hydrogen.

10. The reactor/separator element of claim 1, wherein the reactor/separator element is tapered.

11. The reactor separator element of claim 1, wherein the reactor/separator element is cylindrical.

12. The reactor/separator element of claim 1, wherein the dimensions of the spiral channel change from the first end of the reactor/separator element to the second end.

13. The reactor/separator element of claim 1, wherein a catalyst is present in the central core, the outer layer, throughout the helical channel, or all three.

14. A reaction device comprising a reactor/separator element comprising:
   (a) a central core comprising a gas permeable material, said central core being shaped on the outer surface thereof to define at least one spiral channel extending from a first end of the central core to a second, opposed end of the central core;
   (b) a separation layer, disposed on the central core and conforming to the shape of the outer surface of the central core element, said separation layer being formed from a material selected from the group consisting of (1) materials that are permeable to hydrogen gas under pressure; (2) mixed ionic electronic conductors that are permeable to protons in the absence of an applied potential difference, and (3) proton conducting materials that are permeable to protons in response to an applied potential difference; and
   optionally, (c) an outer layer disposed on the separation layer, said outer layer comprising a gas permeable material,
   wherein the central core and the separation layer, in combination, define at least one spiral gas flow channel extending from the first end of the central core to the second end of the central core; and a housing at least partially enclosing the reactor/separator element to define a helical channel for gas flow.

15. The reaction device of claim 14, wherein the contour of the helical surfaces is such that the cross-sectional area in the radial direction is a specified function of the radius, and more specifically, such that the said cross-sectional area is constant with radius.

16. The reaction device of claim 14, where the cross-section of the flow channel formed by the enclosed helix is shaped to control the space velocity of permeant gas along the length of the spiral channel.

17. The reaction device of claim 14, constructed substantially of ceramic and ceramic composites.

18. The reaction device of claim 14, wherein the separation layer is a dense film of ionically-conducting ceramic coating of about from 10 nanometers to 50 microns in thickness attached to a porous ceramic support.

19. A method for separating hydrogen gas from a mixed gas containing hydrogen gas comprising introducing the mixed gas into the helical channel for gas flow into a reaction device comprising (a) a central core comprising a gas permeable material, said central core being shaped on the outer surface thereof to define at least one spiral channel extending from a first end of the central core to a second, opposed end of the central core;

(b) a separation layer, disposed on the central core and conforming to the shape of the outer surface of the central core element, said separation layer being formed from a material selected from the group consisting of (1) materials that are permeable to hydrogen gas under pressure; (2) mixed ionic electronic conductors that are permeable to protons in the absence of an applied potential difference, and (3) proton conducting materials that are permeable to protons in response to an applied potential difference; and optionally, (c) an outer layer disposed on the separation layer, said outer layer comprising a gas permeable material, wherein the central core and the separation layer, in combination, define at least one spiral gas flow channel extending from the first end of the central core to the second end of the central core; and a housing at least partially enclosing the reactor/separator element to define a helical channel for gas flow, under conditions such that hydrogen gas or protons permeate through the separation layer and recovering separated hydrogen gas from the central core.

20. The method of claim 19, where the mixed gas containing hydrogen is introduced into the helical channel by performing a hydrogen gas-generating reaction within the helical channel.

* * * * *